(12) United States Patent
Ryu et al.

(10) Patent No.: US 7,395,106 B2
(45) Date of Patent: Jul. 1, 2008

(54) WEARABLE PHYSIOLOGICAL SIGNAL DETECTION MODULE AND MEASUREMENT APPARATUS HAVING THE SAME

(75) Inventors: Chang Yong Ryu, Daejeon (KR); Seung Chul Shin, Daejeon (KR); Seung Hoon Nam, Daejeon (KR); Jae Hwan Kang, Daejeon (KR); Yoon Seon Song, Daejeon (KR); Tae Gyu Yim, Daejeon (KR); Seunghwan Kim, Daejeon (KR); Yun Tae Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 320 days.

(21) Appl. No.: 11/085,526

(22) Filed: Mar. 22, 2005

(65) Prior Publication Data

US 2005/0261564 A1  Nov. 24, 2005

(30) Foreign Application Priority Data

May 21, 2004  (KR) ...................... 10-2004-0036186

(51) Int. Cl.
*A61B 5/04* (2006.01)
*A61B 5/06* (2006.01)

(52) U.S. Cl. .................. 600/388; 600/393; 600/395; 600/396

(58) Field of Classification Search ............... 600/388, 600/395, 396
See application file for complete search history.

(56) References Cited

U.S. PATENT DOCUMENTS 4,026,278 A * 5/1977 Ricketts et al. ............. 600/390
4,040,412 A * 8/1977 Sato ........................... 600/391
4,354,509 A * 10/1982 Strahwald et al. ........... 607/153
4,494,553 A    1/1985 Sciarra et al.
4,572,197 A    2/1986 Moore et al.
4,583,547 A    4/1986 Granek et al.
4,709,704 A   12/1987 Lukasiewicz
4,909,260 A    3/1990 Salem et al.
4,966,154 A   10/1990 Cooper et al.
5,050,612 A    9/1991 Matsumura
5,224,479 A    7/1993 Sekine
5,353,793 A   10/1994 Bornn
5,566,671 A * 10/1996 Lyons ......................... 600/372
5,995,861 A   11/1999 Price
6,408,200 B1    6/2002 Takashina
7,062,309 B2 *  6/2006 Ryu et al. ................... 600/372
7,069,089 B2 *  6/2006 Minogue et al. ............ 607/149

FOREIGN PATENT DOCUMENTS

KR    20-0347847    4/2004

* cited by examiner

*Primary Examiner*—Lee S Cohen
(74) *Attorney, Agent, or Firm*—Lowe Hauptman Ham & Berner LLP

(57) ABSTRACT

Provided are a wearable physiological signal detection module and a measurement apparatus having the same. A physiological signal detection module including a measuring electrode implemented by a dry electrode having good conductivity to detect various physiological signals is detachably disposed inside the clothing closely adhered to user's skin. The measuring electrode can be in stable contact with the user's skin as well as the detection module can be conveniently worn for a long time. The various physiological signals detected by the measuring electrodes are wirelessly transmitted to an external device, thereby conveniently monitoring the physiological signal of the user in real time.

19 Claims, 6 Drawing Sheets

WEARABLE PHYSIOLOGICAL SIGNAL DETECTION MODULE AND MEASUREMENT APPARATUS HAVING THE SAME

CROSS-REFERENCE TO RELATED APPLICATION

This application claims priority to and the benefit of Korean Patent Application No. 2004-36186, filed May 21, 2004, the disclosure of which is incorporated herein by reference in its entirety.

BACKGROUND

1. Field of the Invention

The present invention relates to a wearable physiological signal detection module and a measurement apparatus having the same and, more specifically, to a wearable physiological signal detection module and a measurement apparatus having the same, in which a physiological signal detection module including a measuring electrode implemented by a dry electrode having good conductivity to detect various physiological signals is detachably disposed inside the clothing closely adhered to user's skin, and the various physiological signals detected by the measuring electrodes are wirelessly transmitted to an external device, such that the physiological signal of the user is conveniently monitored in real time.

2. Discussion of Related Art

In general, a disposable electrode is adhered on user's skin to measure physiological signals of a human body. This disposable electrode is typically a wet electrode, which is a metal electrode coated with conductive gel, reducing impedance with the skin and facilitating conversion of ion current flowing through the human body into electron current.

However, the conductive gel makes a skin trouble such as flushing or prickling over time. Therefore, the disposable electrode is not suitable for use in the physiological signal measuring apparatus that monitors the skin for a long time (e.g., about 2 hours or more).

The conventional disposable electrode further has a foam pad with an adhesive component, attached to the metal electrode, so that the conventional disposable electrode is well adhered to the skin. It, however, does not provide long-time adhesion to the skin.

Meanwhile, when measurement of the physiological signal is made in a stable condition of the user, only contact of the electrode to the user's skin is required. On the other hand, when the user is in motion, i.e., when the measurement of the physiological signal is made while the user is moving, the secure contact between the skin and the electrode is required to obtain physiological signals with less noise. In other words, when the skin and the electrode are separated from each other due to motion, the signal input to the physiological signal measuring apparatus may be saturated.

SUMMARY OF THE INVENTION

The present invention has been made to solve the aforementioned problems. The present invention is directed to a wearable physiological signal detection module and a measurement apparatus having the same, in which a physiological signal detection module including a measuring electrode implemented by a dry electrode having good conductivity to detect various physiological signals is detachably disposed inside the clothing closely adhered to user's skin, and the various physiological signals detected by the measuring electrodes are wirelessly transmitted to an external device, such that the measuring electrode is in stable contact with the user's skin, the detection module is conveniently worn for a long time, and the physiological signal of the user is conveniently monitored in real time.

In one aspect of the present invention, there is provided a wearable physiological signal measuring apparatus comprising: a clothing having flexibility to be closely adhered to user's skin; at least one physiological signal detection module detachably disposed inside the clothing comprising: a measuring electrode closely adhered to the skin for detecting various physiological signals of the user; a body having a space portion with an open end for containing the measuring electrode and a given passing-through hole at one face for exposing a part of the measuring electrode; and a supporting member provided in the space portion of the body to support the measuring electrode; and a physiological signal measuring module electrically connected with the measuring electrode to convert the various physiological signals into digital physiological signals and to process the digital physiological signals for obtain various physiological information data.

In another aspect of the present invention, there is provided a wearable physiological signal detection module comprising: a measuring electrode closely adhered to user's skin for detecting various physiological signals of the user; a body having a space portion with an open end for containing the measuring electrode and a passing-through hole at one face for exposing a part of the measuring electrode; and a supporting member provided in the space of the body to support the measuring electrode, wherein the wearable physiological signal detection module is detachably disposed inside of a clothing having flexibility closely adhered to the user's skin.

The physiological signal measuring means comprises: an amplification unit for amplifying the various physiological signals received from the measuring electrodes; a filtering unit for removing various noises from the various physiological signals amplified through the amplification unit to obtain desired physiological signals; and a control unit for receiving the various physiological signals from the filtering unit, converting the various physiological signals into digital physiological signals, and processing the digital physiological signals to obtain the various physiological information data.

BRIEF DESCRIPTION OF THE DRAWINGS

The above and other features of the present invention will be described in reference to certain exemplary embodiments thereof with reference to the attached drawings, in which.

DETAILED DESCRIPTION OF THE PREFERRED EMBODIMENTS

Preferred embodiment of the present invention will now be described with reference to the attached drawings. However, the present invention is illustrative only, but not limited hereto.

Figure 1:
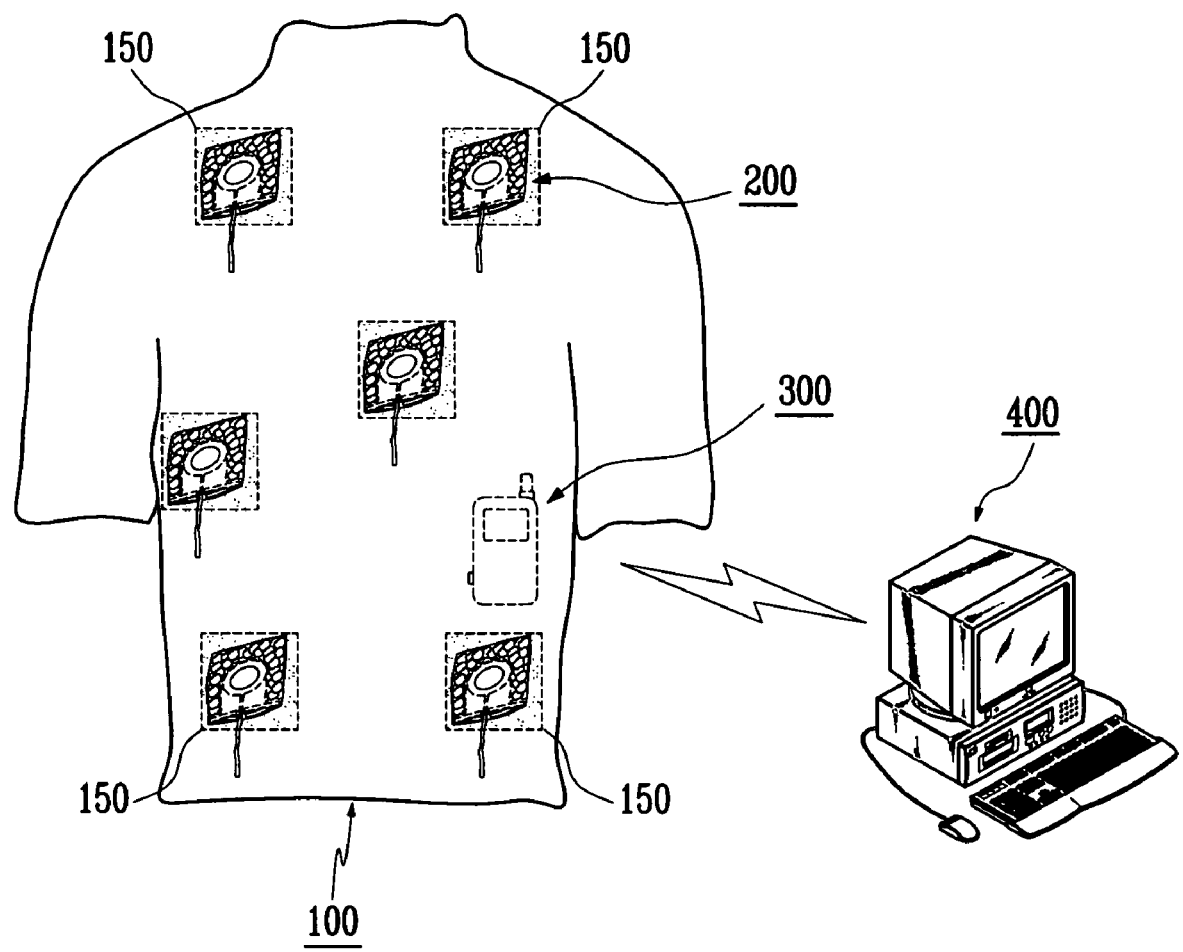
FIG. 1 is a schematic diagram illustrating a wearable physiological signal measuring apparatus according to an embodiment of the present invention.

FIG. 1 is an entire schematic diagram illustrating a wearable physiological signal measuring apparatus according to an embodiment of the present invention.

Referring to FIG. 1, the wearable physiological signal measuring apparatus includes a clothing 100; physiological signal detection modules 200 detachably disposed inside the clothing 100 for detecting various physiological signals, such as electrocardiogram (ECG), electrodermal activity (EDA), body fat, and respiration; and a physiological signal measuring module 300 disposed at an appropriate place of the clothing for receiving the various detected physiological signals from the physiological signal detection modules 200, processing the received physiological signals to obtain physiological information data, and then, wirelessly transmitting the physiological information data to an external device 400.

Here, the clothing 100 is implemented by a highly elastic flexible jacket to be closely adhered to user's skin. The clothing 100 has at least one "loop" surface 150 of hook and loop fastener (VELCRO®) at inner proper places, i.e., at appropriate places for measuring the physiological signals to detachably engage with a "hook" surface 214 of hook and loop fastener (in FIG. 3) of the physiological signal detection module 200.

Although the physiological signal measuring module 300 is preferably inserted and mounted into a pouch (not shown) formed inside or outside of the clothing 100, the present invention is not limited hereto. The physiological signal measuring module 300 may be firmly fixed to the inside of the clothing 100 using a hook and loop fastener.

The external device 400 is a device capable of wirelessly receiving and managing physiological information data from the physiological signal measuring module 300 and is preferably implemented with a personal computer, a mobile phone, a personal digital assistant (PDA), or the like.

For example, when the external device 400 is implemented with the PDA, it may be a PDA of model No. YOPY3700 available from Gmate Co., which is operated by a 32-bit RISC microprocessor of Intel StrongARM SA-1110 and uses ARM Linux (Linupy™) as an operation system. In addition, the PDA has a phone module supporting CDMA2000 1× and a CF slot into which a wireless LAN card is inserted to support Internet at a hot spot where an access point (AP) is disposed.

In addition, the PDA may use a Bluetooth CompactFlash card available from SysOnChip Co. for wireless communication with the physiological signal measuring module 300, and may port and use an open source based Bluez stack (official Linux Bluetooth protocol stack). The PDA has a user consol—which may be built by GTX version 1.2 based on Linux version 2.4 OS.

Meanwhile, the PDA as described above is able to store the physiological information data transmitted from the physiological signal measuring module 300, and display the physiological information data of any selected channel, e.g., electrocardiogram.

Figure 2:
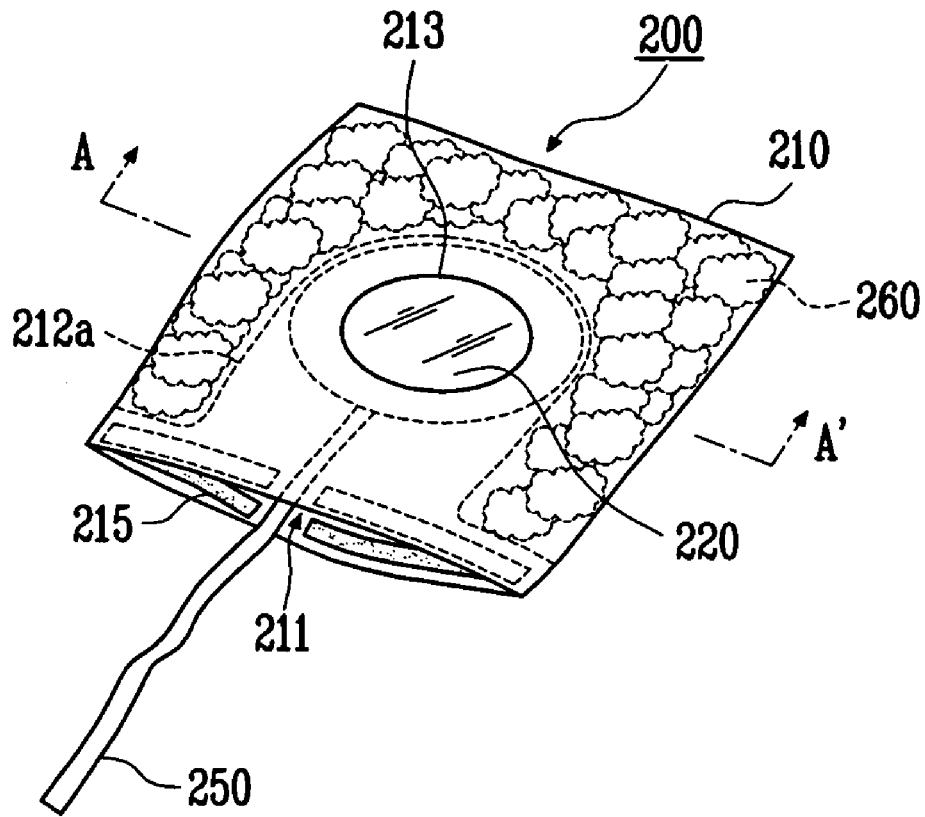
FIG. 2 is a perspective view showing a front face of a wearable physiological signal detection module according to an embodiment of the present invention.
Figure 3:
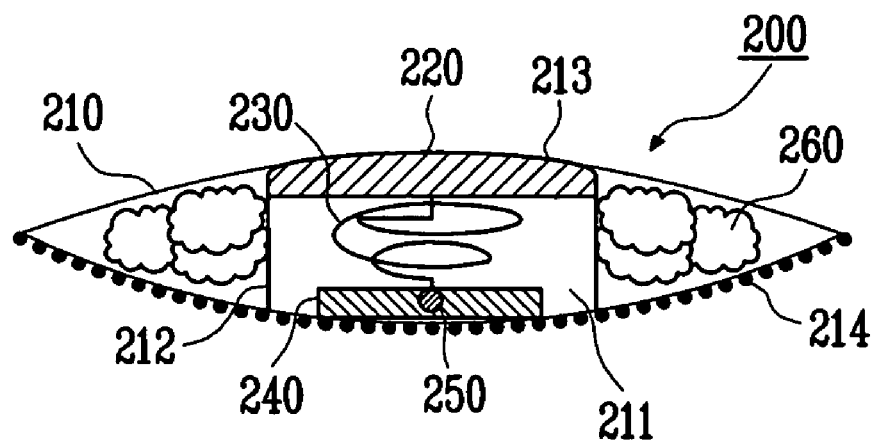
FIG. 3 is a cross-sectional view taken along the A-A' line of FIG. 2.
Figure 4:
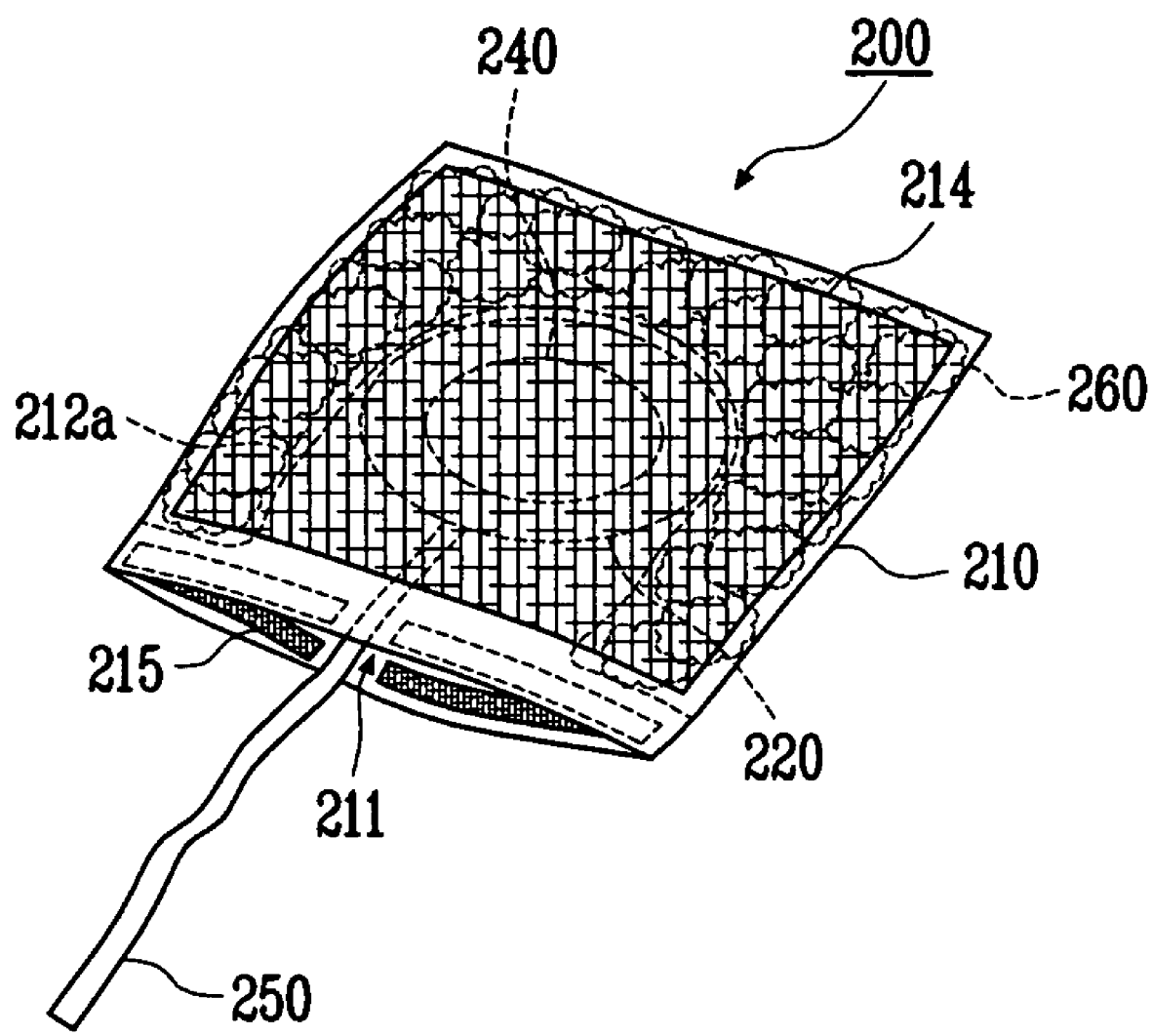
FIG. 4 is a perspective view showing an rear face of a wearable physiological signal detection module according to an embodiment of the present invention.

FIG. 2 is a perspective view showing an front face of a wearable physiological signal detection module 200 according to an embodiment of the present invention, FIG. 3 is a cross-sectional view taken along the A-A' line of FIG. 2, and FIG. 4 is a perspective view showing a rear face of the wearable physiological signal detection module 200 according to an embodiment of the present invention;

Referring to FIGS. 2 to 4, the physiological signal detection module 200 according to an embodiment of the present invention comprises a body 210, a measuring electrode 220, an elastic member 230, a supporting member 240, an electrical cable 250, and cushion members 260.

The body 210 constitutes an entire pouch-shaped body made of a soft fiber material. The body 210 has a predetermined space portion 211 with an open end. In order to form the space portion 211, a space forming member 212 made of the same material as that of the body 210 is positioned into the body 210 and is sewed along a fixed line 212a provided at the front and rear faces thereof.

Further, a predetermined passing-through hole 213 is formed at one face, i.e., the front face, of the body 210 to expose a part of the measuring electrode 220, and a hook surface 214 of hook and loop fastener is formed at the other face thereof, i.e., the rear face, to detachably engage with a loop surface 150 of hook and loop fastener of the clothing 100.

In addition, an open and close portion 215 of a hook and loop fastener strip in the form of hook and loop portions is formed at an open portion of the space portion 211 to fix the electrical cable 250 electrically connected to the measuring electrode 220 and facilitate opening and closing.

The measuring electrode 220 is inserted into the body 210 through the opening of the space portion 211, and is in direct contact with the user's skin to detect various physiological signals. The measuring electrode 220 is preferably implemented with a dry electrode made of metal having good conductivity (e.g., Au, Pt and Ag/AgCl)

The elastic member 230 is disposed inside the space portion 211, namely, below the measuring electrode 220 and functions to support the measuring electrode 220 to be closely adhered to the user's skin. The elastic member 230 is preferably implemented by a helical spring having a predetermined elastic restoration force.

In other words, the helical spring does not contact with each other because of its helical-shape even though the spring is compressed under external pressure, which makes it possible to effectively detect the physiological signal without distortion.

Further, it is desirable that one end of the elastic body 230 is fixedly disposed to the rear face of the measuring electrode 220, and the other end of the elastic member 230 is fixedly disposed to the front face of the supporting member 240.

The supporting member 240 is disposed below the measuring electrode 220 and the elastic member 230 to support the elastic member 230 against the pressure exerted through the elastic member 230 from the measuring electrode 220. The supporting member 240 is preferably formed of plastic, e.g., lightweight plastic.

The electrical cable 250 is electrically connected to the measuring electrode 220 for transmitting the physiological signal detected through the measuring electrode 220 to the physiological signal measuring module 300, and is pulled out through the opening of the space portion 211 with the supporting member 240 connected to the electrical cable 250.

The cushion members 260 are used to maintain overall elasticity of the body 210 and improve close adherence to the skin. The cushion members 260 are provided in the body 210 to surround the space portion 211. The cushion members 260 are preferably formed of elastic fiber material, such as cotton and sponge.

Figure 5:
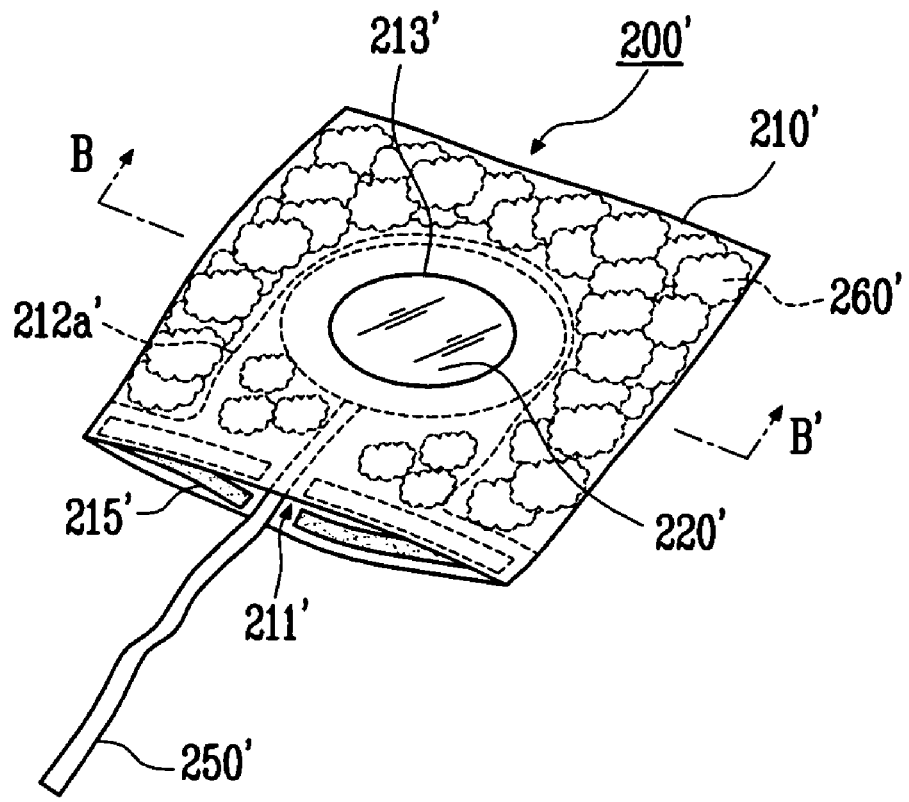
FIG. 5 is a perspective view showing a front face of a wearable physiological signal detection module according to another embodiment of the present invention.
Figure 6:
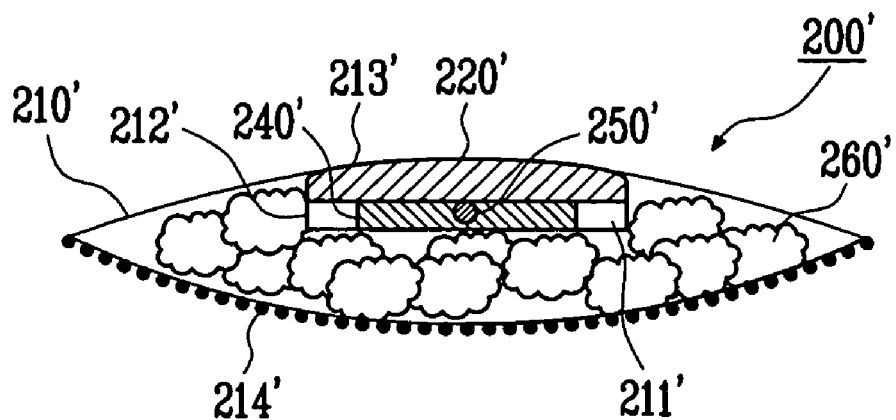
FIG. 6 is a cross-sectional view taken along the B-B' line of FIG. 5.
Figure 7:
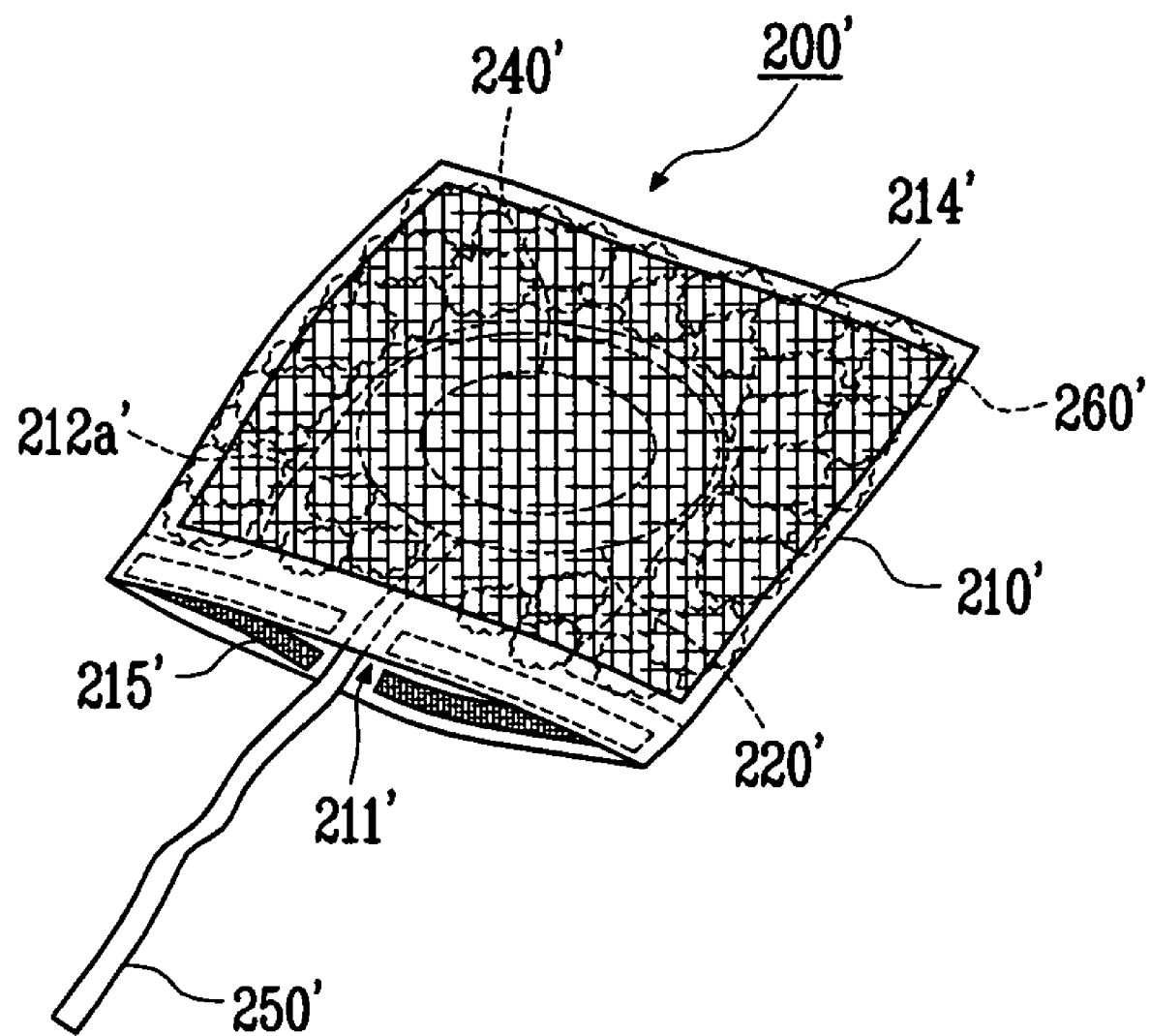
FIG. 7 is a perspective view showing a rear face of a wearable physiological signal detection module according to another embodiment of the present invention.

FIG. 5 is a perspective view showing an front face of a wearable physiological signal detection module according to another embodiment of the present invention, FIG. 6 is a cross-sectional view taken along the B-B' line of FIG. 5, and FIG. 7 is a perspective view showing a rear face of a wearable physiological signal detection module according to another embodiment of the present invention.

The physiological signal detection module 200' according to another embodiment of the present invention has the same configuration as that of the physiological signal detection module 200 according to the above-described embodiment of the present invention, for example, a measuring electrode 220', an open and close portion 215', an electrical cable 250', and the like. Accordingly, the description thereon will be omitted herein.

Referring to FIGS. 5 to 7, the physiological signal detection module 200' according to another embodiment of the present invention includes a body 210', a measuring electrode 220', a supporting member 240', an electrical cable 250' and cushion members 260'.

The body 210' has an entire pouch-shaped body made of soft fiber material. The body 210' has a predetermined space portion 211' with an open end therein. In order to form the space portion 211', a space forming member 212' made of the same material as that of the body 210' is positioned into the body 210' and is sewed along a fixed line 212a' provided at the front face thereof.

In addition, a predetermined passing-through hole 213' is formed at one face, i.e., the front face, of the body 210' to expose a part of the measuring electrode 220', and a hook surface 214' of hook and loop fastener is formed at the other end, i.e., the rear face, to detachably engage with a loop surface 150 of hook and loop fastener of the clothing 100.

The supporting member 240' is disposed below the measuring electrode 220' to support the measuring electrode 220' against the pressure exerted from the measuring electrode 220'. The supporting member 240' is preferably formed of plastic, e.g., lightweight plastic.

The cushion members 260' are used to maintain overall elasticity of the body 210' and improve close adherence to the skin, as a substitute for the elastic member 230 of the physiological signal detection module 200 according to the above-described embodiment of the present invention. The cushion members 260' are provided in the body 210' to surround the space portion 211'. The cushion members 260' are preferably formed of elastic fiber, such as cotton and sponge.

The physiological signal detection module 200 configured as described above requires a plurality of measuring electrodes 220 or 220' to measure, for example, electrocardiogram (ECG) among various physiological signals of the user. Preferably, six measuring electrodes for measurement are located as follows: right arm (RA) and left arm (LA) located at boundaries between chests and shoulders in the right and left sides, respectively; V1 located between fourth and fifth left ribs from the top; V6 located between fifth and sixth right ribs; and ground and left leg (LL) located at intersect points between RA and LA located at the left and right sides of the navel and the vertical axis.

The physiological signals obtained by these six measuring electrodes are converted into 12 lead signals through matrix conversion and is used for ECG analysis. Further, the respiration of the user can be measured at RA and V6 of the ECG measuring electrodes using an impedance method.

Further, the components of the physiological signal detection module 200 of the present invention other than the measuring electrodes 220 or 220' may be fabricated as disposables.

Figure 8:
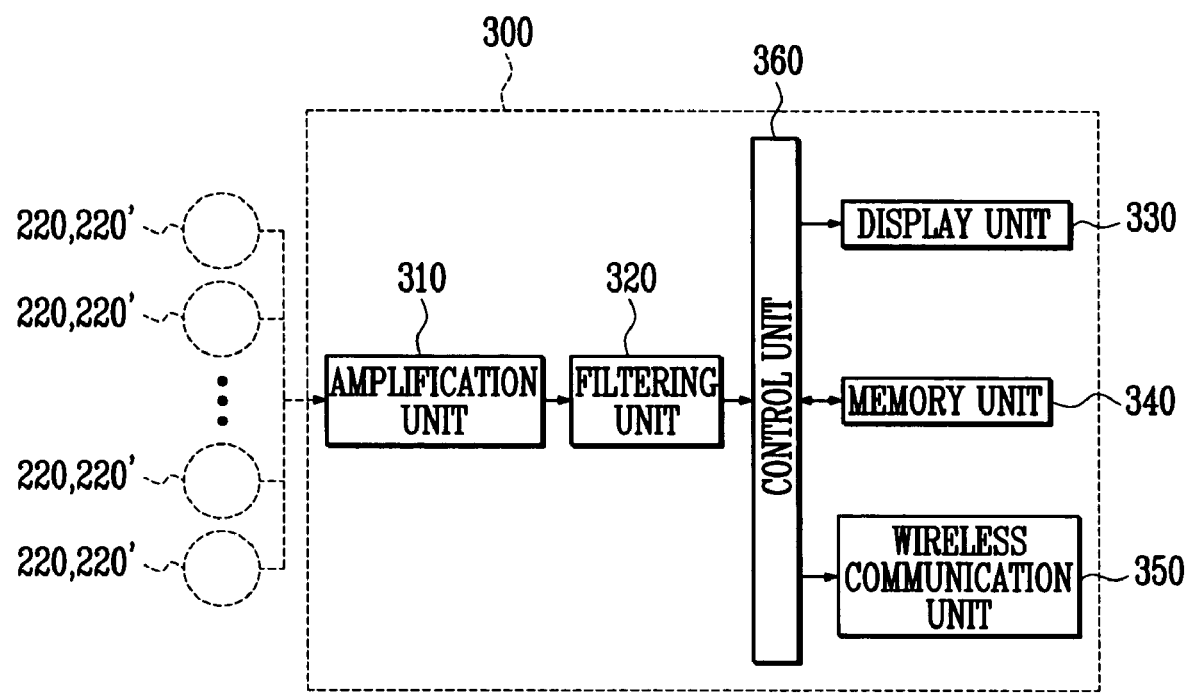
FIG. 8 is a schematic block diagram illustrating a physiological signal measuring module according to an embodiment of the present invention.

FIG. 8 is a schematic block diagram illustrating a physiological signal measuring module according to an embodiment of the present invention.

Referring to FIG. 8, the physiological signal measuring module 300 according to an embodiment of the present invention includes an amplification unit 310, a filtering unit 320, a display unit 330, a memory unit 340, a wireless communication unit 350, and a control unit 360.

The amplification unit 310 functions to amplify weak physiological signals output from the measuring electrodes 220 or 220'.

The filtering unit 320 functions to output desired physiological signals by removing various noises from the signals amplified by the amplification unit 310.

The display unit 330 functions to visually display various physiological information data obtained by the control unit 360 to the user.

The memory unit 340 functions to store the various physiological signals and information data obtained by the control unit 360.

The wireless communication unit 350 functions to wirelessly transmit the various physiological signals and information data to the external device 400 under the control of the control unit 360. Specifically, the wireless communication unit 350 is preferably implemented with a Hitachi Maxell Bluetooth module having BlueCore2 available from CSR Co.

The control unit 360 functions to receive the physiological signals output from the filtering unit 320, convert the physiological signals into digital physiological signals using a typical A/D converter (not shown), and processing the converted digital physiological signals to obtain various physiological information data.

The physiological signal measuring module 300 configured as described above can wirelessly transmit physiological signals and information data of the user to the external device 400 in real time, and the external device 400 transmits the physiological signals and information data to a physiological signal monitoring center (not shown) in a medical institution through for example Internet to monitor health status of the user.

The physiological signal measuring module 300 further includes an event button. When the user presses this button under an emergency situation, the physiological signal measuring module 300 may automatically measure and transmit various physiological signals, provide a corresponding service to take the emergency measures, and measure the physiological signals at a time desired by the user or a doctor.

In addition, the physiological signal measuring module 300 can be connected to a wearable apparatus for measuring physiological signals such as temperature, blood pressure, and oxygen saturation as well as physiological signals that can be measured by the measuring electrodes 220 or 220', and it can be built with an acceleration measuring sensor for measuring the user motion, e.g., 2-axis accelerations such as sensor ADXL250, ADXL202 (Analog device) and KXG30-L20 (Kionix).

Here, in order to measure the user temperature, a predetermined temperature sensor such as LM35CAZ (National Semiconductor) having accuracy of ±0.2° C. at room temperature (+25° C.) can be used, which is preferably located in the armpit of the user.

In addition, the physiological signal measuring module 300 can be connected to a PDA, a Bluetooth, or a wireless LAN having a function of cellular phone to directly transmit physiological signals and information data to the medical monitoring service center, and store the physiological signals and information data into memories when the wireless communication is not available to transmit through the wireless communication unit 350 later.

In the wearable physiological signal measuring apparatus as described above according to the present invention, a physiological signal detection module having a measuring electrode implemented by a dry electrode having a good conductivity is detachably disposed inside the clothing closely adhered to user's skin to detect various physiological signals and various physiological signals detected from the measuring electrodes are wirelessly transmitted to the external device, thereby causing the measuring electrode to stably contact with the user's skin and to wear comfortably for a long time, and facilitating a monitor on the physiological signal of the user in the real time.

The wearable physiological signal measuring apparatus of the present invention as described above has the following advantages: First, a physiological signal detection module including a measuring electrode is detachably disposed inside the clothing closely adhered to user's skin to detect various physiological signals, and the various physiological signals detected by the measuring electrodes are wirelessly transmitted to the external device, thereby conveniently monitoring the physiological signal of the user in real time.

Second, the soft loop surface of hook and loop fastener is formed inside the clothing having flexibility to be detachable to the hook surface of hook and loop fastener of the physiological signal detection module, such that the measuring electrode is in stable contact with the user's skin and is conveniently worn for a long time. In addition, the physiological signal detection module can be disposed at an exact physiological signal measuring position according to a figure of the user.

Third, by using the measuring electrode of the physiological signal detection module as a dry electrode formed of metal having good conductivity, a skin trouble does not occur to the user even though the measurement of the physiological signals is made for a long time.

Fourth, by comprising the elastic member, i.e., the helical spring or cushion members, having a predetermined elastic restoration force below the measuring electrode provided in the space of the body, the close adherence between the user's skin and the measuring electrode can be effectively improved and the physiological signals can be detected without distortion.

Fifth, by including the cushion members having predetermined elastic restoration forces in the body to surround the space of the body, the overall elasticity of the body can be maintained and the close adhesion to the skin can be further improved.

Sixth, since the body of the measuring electrode detection module and the clothing made of fiber material can be separately washed, a contaminant produced due to a long time wearing can be easily removed to keep clean all the time.

Although the wearable physiological signal detection module and measuring apparatus according to the preferred embodiments of the present invention has been described, the present invention is not limited hereto, but a variety of modification can be made within the claims, the detailed description of the invention, and the attached drawings, which are also included in the present invention.

What is claimed is:

1. A wearable physiological signal measuring apparatus comprising:
   a clothing having flexibility to be closely adhered to user's skin;
   at least one physiological signal detection module detachably disposed inside the clothing comprising:
   at least one measuring electrode adapted to closely adhere to the skin for detecting various physiological signals of the user;
   a body having a space portion with an open end for containing the at least one measuring electrode and a given passing-through hole at one face for exposing a part of the at least one measuring electrode; and
   a supporting member provided in the space portion of the body to support the at least one measuring electrode; and
   a physiological signal measuring module electrically connected with the at least one measuring electrode to convert the various physiological signals into digital physiological signals and to process the digital physiological signals to obtain various physiological information data.

2. The apparatus according to claim 1, wherein the at least one measuring electrode is a dry electrode formed of any one metal of Au, Pt and Ag/AgCl.

3. The apparatus according to claim 1, wherein a loop surface of hook and loop fastener is formed in a predetermined region inside the clothing, and a hook surface of hook and loop fastener is formed at the other face of the body to detachably engage with the loop surface of hook and loop fastener.

4. The apparatus according to claim 1, wherein the body is made of fiber material.

5. The apparatus according to claim 1, further comprising an elastic member having a predetermined elastic restoration force between the at least one measuring electrode and the supporting member to closely adhere the at least one measuring electrode to the user's skin.

6. The apparatus according to claim 5, wherein the elastic member is a helical spring.

7. The apparatus according to claim 1, further comprising cushion members provided in the body for maintaining overall elasticity and surrounding the space portion to improve close adhesion to the skin.

8. The apparatus according to claim 7, wherein the cushion members each has a predetermined elastic restoration force and is made of fiber material.

9. The apparatus according to claim 1, wherein the physiological signal measuring module comprises:
   an amplification unit for amplifying the various physiological signals received from the at least one measuring electrode;
   a filtering unit for removing various noises from the various physiological signals amplified through the amplification unit to obtain desired physiological signals; and
   a control unit for receiving the various physiological signals from the filtering unit, converting the various physiological signals into digital physiological signals, and processing the digital physiological signals to obtain the various physiological information data.

10. The apparatus according to claim 9, further comprising a wireless communication unit for transmitting the various physiological signals and the various physiological information data to an external device under the control of the control unit.

11. The apparatus according to claim 9, further comprising a display unit for displaying the various physiological signals and the various physiological information data obtained by the control unit.

12. The apparatus according to claim 9, further comprising a memory unit for storing the various physiological signals and the various physiological information data obtained by the control unit.

13. A wearable physiological signal detection module comprising:
- at least one measuring electrode adapted to physically contact a user's skin for detecting various physiological signals of the user;
- a body having a space portion with an open end for containing the at least one measuring electrode and a passing-through hole at one face for exposing a part of the at least one measuring electrode; and
- a supporting member provided in the space portion of the body to support the at least one measuring electrode, wherein the wearable physiological signal detection module is adapted to be detachably disposed inside of a clothing having flexibility to be closely adhered to the user's skin.

14. The module according to claim 13, wherein a loop surface of hook and loop fastener is formed in a predetermined region inside the clothing, and a hook surface of hook and loop fastener is formed at the other face of the body to detachably engage with the loop surface of hook and loop fastener.

15. The module according to claim 13, wherein the body is largely made of fiber material.

16. The module according to claim 13, further comprising an elastic member having a predetermined elastic restoration force between the at least one measuring electrode and the supporting member to closely adhere the at least one measuring electrode to the user's skin.

17. The module according to claim 16, wherein the elastic member is a helical spring.

18. The module according to claim 13, further comprising cushion members provided in the body for maintaining overall elasticity and surrounding the space portion to improve close adhesion to the skin.

19. The module according to claim 18, wherein the cushion members each has a predetermined elastic restoration force and is formed of fiber material.

* * * * *